(12) United States Patent
Paul et al.

(10) Patent No.: US 7,150,759 B2
(45) Date of Patent: Dec. 19, 2006

(54) MULTI-MECHANISTIC ACCOMMODATING INTRAOCULAR LENSES

(75) Inventors: Marlene L. Paul, Laguna Niguel, CA (US); Daniel G. Brady, San Juan Capistrano, CA (US); Michael Lowery, Vista, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 204 days.

(21) Appl. No.: 10/661,410

(22) Filed: Sep. 12, 2003

(65) Prior Publication Data

US 2004/0127984 A1    Jul. 1, 2004

Related U.S. Application Data

(63) Continuation-in-part of application No. 10/341,701, filed on Jan. 14, 2003, now Pat. No. 7,025,783.

(60) Provisional application No. 60/372,309, filed on Apr. 12, 2002, provisional application No. 60/348,705, filed on Jan. 14, 2002.

(51) Int. Cl.
   *A61F 2/16* (2006.01)

(52) U.S. Cl. .................. 623/6.22; 623/6.23; 623/6.24; 623/6.27; 623/6.37; 623/6.38; 623/6.4; 623/6.51

(58) Field of Classification Search ............... 623/6.13, 623/6.15, 6.22, 6.23, 6.24, 6.27, 6.28, 6.29, 623/6.3, 6.37, 6.38, 6.39, 6.4, 6.43, 6.51, 623/6.56, 6.11
See application file for complete search history.

(56) References Cited

U.S. PATENT DOCUMENTS

| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,673,616 A | 7/1972 | Federov et al. |

(Continued)

FOREIGN PATENT DOCUMENTS

AU    3225789    10/1989

(Continued)

OTHER PUBLICATIONS

U.S. Appl. No. 10/280,918, filed Aug. 5, 2003.

(Continued)

*Primary Examiner*—Eduardo C. Robert
*Assistant Examiner*—Thomas J. Sweet
(74) *Attorney, Agent, or Firm*—Advanced Medical Optics, Inc.

(57) ABSTRACT

An intraocular lens (IOL) includes an optic for focusing light and an accommodation assembly for axially moving and/or deforming the optic in response to naturally occurring actions of the eye, thus allowing a patient to more effectively focus on near objects. In addition, the optic may be multi-focal or aspheric, wherein the maximum add power of the lens is combined with the increase in diopter power obtained through axial movement and/or deformation of the optic, resulting in enhanced accommodation.

26 Claims, 4 Drawing Sheets

U.S. PATENT DOCUMENTS

| | | |
|---|---|---|
| 3,693,301 A | 9/1972 | Lemaltre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,244,060 A | 1/1981 | Hoffer |
| 4,244,597 A * | 1/1981 | Dandl .................. 280/473 |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsnetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | DeCarle |
| 4,710,194 A | 12/1987 | Kelman |
| 4,720,286 A | 1/1988 | Bailey et al. |
| 4,725,278 A | 2/1988 | Shearing |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,152,789 A * | 10/1992 | Willis .................. 623/6.4 |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |

| | | |
|---|---|---|
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,998 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Meneles et al. |
| 5,876,442 A | 3/1999 | Lipshitz et al. |
| 5,898,473 A | 4/1999 | Seidner et al. |
| 5,968,094 A | 10/1999 | Werblin et al. |
| 6,013,101 A | 1/2000 | Israel |
| 6,051,024 A | 4/2000 | Cumming |
| 6,096,078 A | 8/2000 | McDonald |
| 6,110,202 A | 8/2000 | Barraquer et al. |
| 6,117,171 A | 9/2000 | Skottun |
| 6,136,026 A | 10/2000 | Israel |
| 6,152,958 A | 11/2000 | Nordan |
| 6,176,878 B1 | 1/2001 | Gwon et al. |
| 6,197,058 B1 | 3/2001 | Portney |
| 6,200,342 B1 | 3/2001 | Tassignon |
| 6,217,612 B1 | 4/2001 | Woods |
| 6,231,603 B1 * | 5/2001 | Lang et al. ............ 623/6.37 |
| 6,299,641 B1 | 10/2001 | Woods |
| 6,302,911 B1 | 10/2001 | Hanna |
| 6,322,589 B1 | 11/2001 | Cumming |
| 6,406,494 B1 | 6/2002 | Laguette et al. |
| 6,443,985 B1 | 9/2002 | Woods |
| 6,485,516 B1 | 11/2002 | Boehm |
| 6,488,708 B1 | 12/2002 | Sarfarazi |
| 6,503,276 B1 | 1/2003 | Lang et al. |
| 6,524,340 B1 | 2/2003 | Israel |
| 6,551,354 B1 | 4/2003 | Ghazizadeh et al. |
| 6,554,859 B1 | 4/2003 | Lang et al. |
| 6,558,420 B1 | 5/2003 | Green |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B1 | 10/2003 | Laguette |
| 6,638,306 B1 * | 10/2003 | Cumming ............ 623/6.37 |
| 6,645,246 B1 | 11/2003 | Weinschenk, III et al. |
| 6,660,035 B1 | 12/2003 | Lang et al. |
| 6,749,633 B1 | 6/2004 | Lorenzo et al. |
| 6,749,634 B1 | 6/2004 | Hanna |
| 6,855,164 B1 * | 2/2005 | Glazier .................. 623/6.37 |
| 7,018,409 B1 | 3/2006 | Glick et al. |
| 7,025,783 B1 | 4/2006 | Brady et al. |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0188351 A1 | 12/2002 | Laguette |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0187505 A1 | 10/2003 | Liao |
| 2003/0204254 A1 | 10/2003 | Peng et al. |
| 2003/0204255 A1 | 10/2003 | Peng et al. |
| 2004/0054408 A1 * | 3/2004 | Glick et al. ............ 623/6.24 |
| 2004/0082993 A1 | 4/2004 | Woods |
| 2004/0082994 A1 | 4/2004 | Woods et al. |
| 2004/0111153 A1 | 6/2004 | Woods et al. |
| 2004/0158322 A1 | 8/2004 | Shen |
| 2004/0181279 A1 | 9/2004 | Nun |
| 2004/0215340 A1 | 10/2004 | Mebner et al. |
| 2005/0085907 A1 | 4/2005 | Hanna |
| 2005/0131535 A1 | 6/2005 | Woods |
| 2005/0137703 A1 | 6/2005 | Chen |

FOREIGN PATENT DOCUMENTS

| | | |
|---|---|---|
| CH | 681687 A5 | 5/1993 |
| DE | 2702117 | 7/1978 |
| DE | 2702117 A1 | 7/1978 |
| DE | 3246306 | 6/1984 |
| DE | 3246306 A1 | 6/1984 |
| DE | 4038088 | 6/1992 |
| DE | 4038088 A1 | 6/1995 |
| EP | 0064812 | 11/1982 |
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0 356 050 | 2/1990 |
| EP | 0488835 | 6/1992 |
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| EP | 0766540 B1 | 4/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 93/05733 | 4/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/27825 | 8/1997 |
| WO | 97/43984 | 11/1997 |
| WO | 98/56315 | 12/1998 |
| WO | 00/66039 | 11/2000 |
| WO | WO 01/19288 A1 | 3/2001 |
| WO | 01/34066 | 5/2001 |
| WO | 01/34067 | 5/2001 |

| | | |
|---|---|---|
| WO | WO 02/19949 A2 | 3/2002 |
| WO | WO 03/059208 A2 | 7/2003 |
| WO | WO 05018504 A1 | 7/2004 |
| WO | 05/018504 | 3/2005 |
| ZA | 888414 | 10/1988 |
| ZA | 888414 | 11/1988 |

OTHER PUBLICATIONS

U.S. Appl. No. 10/280,937, filed Oct. 25, 2005.
Menzo et al. *Endothelial study of iris-claw phakic lens: four year follow-up.* J. Cataract Refract. Surg., Aug. 24, 1998.
Fechner et al. *Iris-claw lens in phakic eyes to correct hyperopia: preliminary study.* J. Cataract Refract. Surg., Jan. 24, 1998.
AMO Specs, Model AC-218, 1992.
Chiron Vision, Nuvita, Mar. 20, 1997.
Mandell, *Contact Lens Practice*, 4th Ed.
Partial Program Re: ASCRS Symposium showing video tape between Apr. 10-14, 1999.
Video tape "New elliptical accom. IOL for cataract surgery" shown at ASCRS Symposium on Apr. 10, 1999.
Thornton, *Accommodation in Pseudophakia*, 25, p. 159.

\* cited by examiner

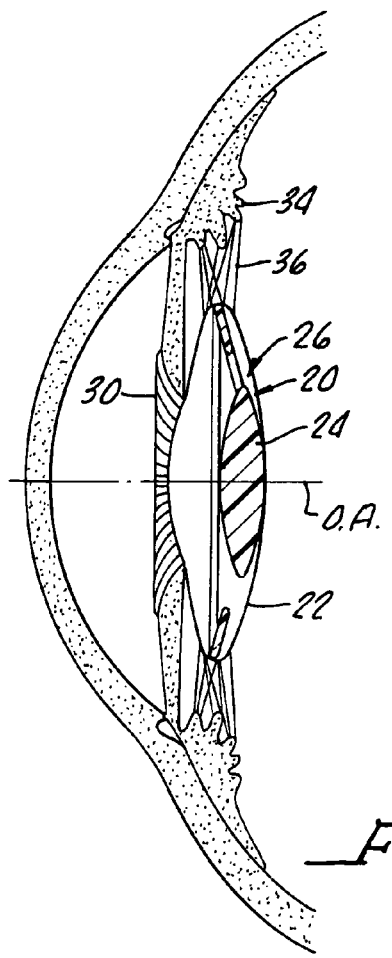
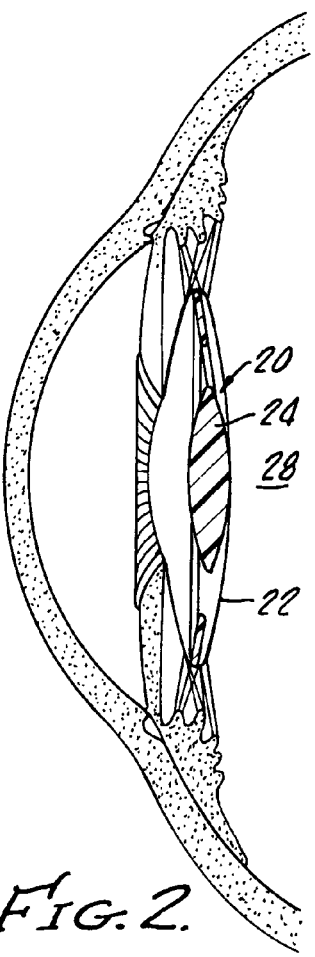
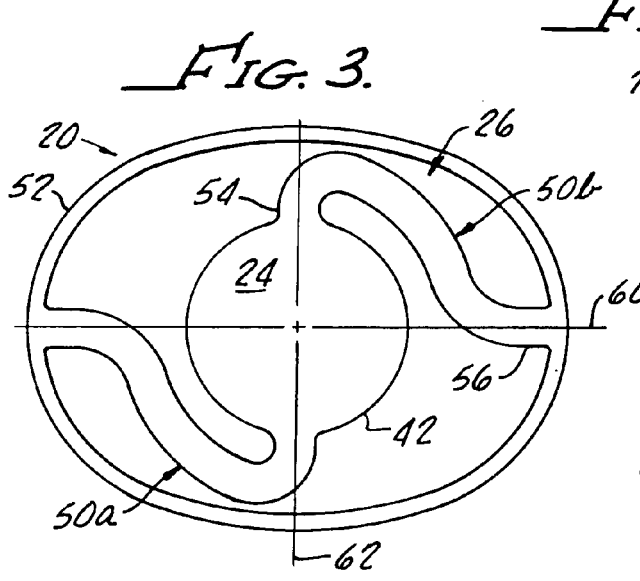
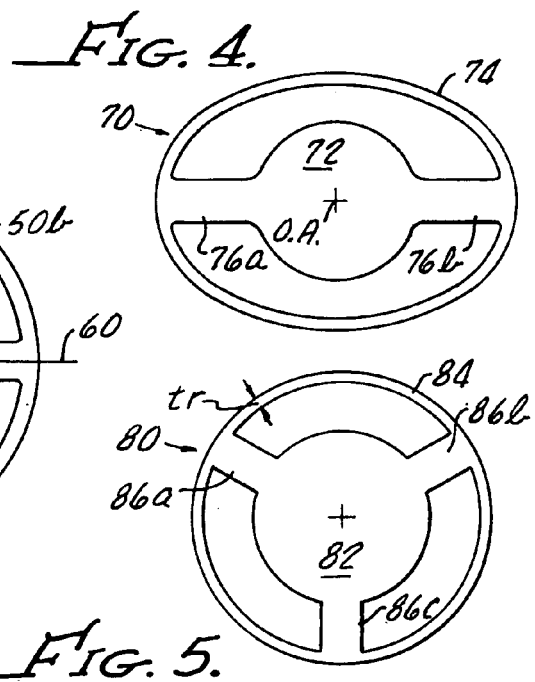

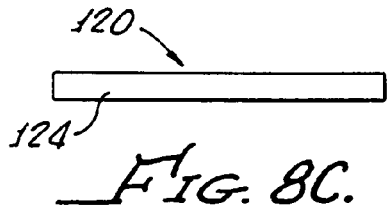
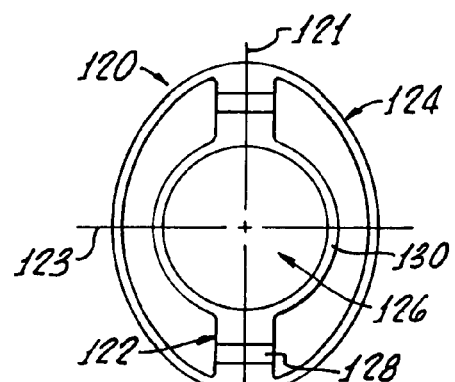
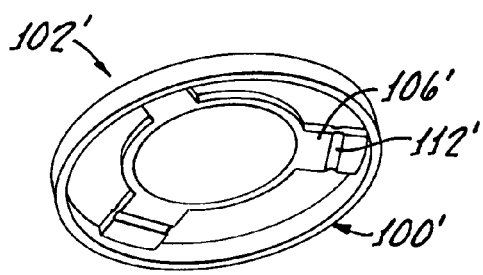
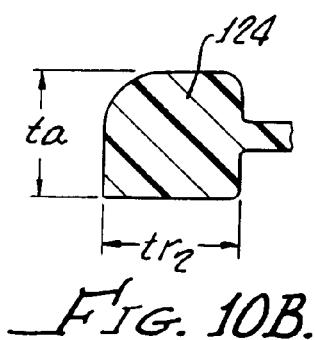
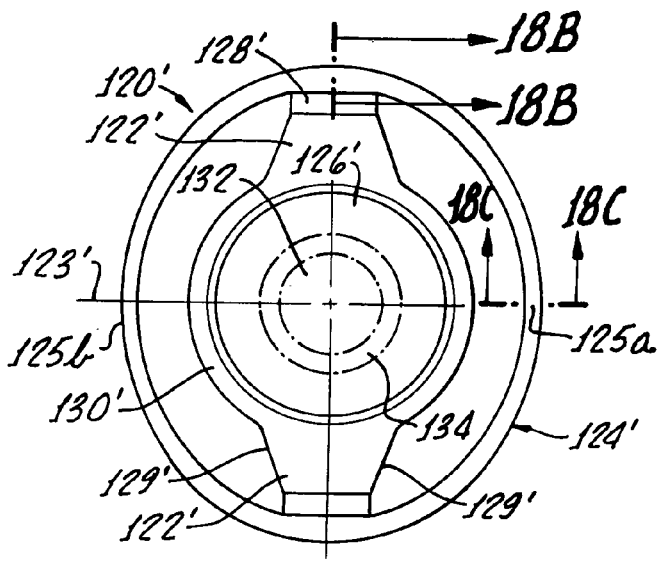
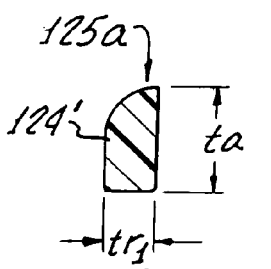

MULTI-MECHANISTIC ACCOMMODATING INTRAOCULAR LENSES

This application is a Continuation-In-Part application of U.S. patent application Ser. No. 10/341,701, filed Jan. 14, 2003 now U.S. Pat. No. 7,025,783, which claimed the benefit of provisional application Ser. No. 60/348,705, filed Jan. 14, 2002, and provisional application Ser. No. 60/372,309, filed Apr. 12, 2002. The disclosures of the aforementioned application and each of the provisional applications are incorporated in their entireties herein by reference.

BACKGROUND OF THE INVENTION

The present invention relates to intraocular lenses (IOLs). More particularly, the present invention relates to IOLs that provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis.

IOLs which achieve accommodation by changing shape generally fall into one of two categories. In the first category, external means, such as magnetic or electric fields, inflation devices, or micromotors, are used to change the curvature of a deformable optic. In the second category, a force transfer assembly is provided for transferring the natural forces exerted by the eye to a composite optic including two or more portions with differing mechanical and/or optical properties.

Examples of the first category (i.e. externally actuated) shape-changing accommodating IOLs are found in Schachar U.S. Pat. No. 4,373,218, Kern U.S. Pat. No. 4,601,545, Pfoff U.S. Pat. No. 4,816,031, Wiley U.S. Pat. Nos. 5,066,301, 5,108,429, and 5,203,788, and Wiley et al. U.S. Pat. No. 5,171,266. The disclosures of each of these patents are incorporated herein in their entireties by reference.

Examples of the second category of shape-changing (i.e. naturally actuated) accommodating IOLs are found in Sulc et al. U.S. Pat. No. 4,994,083 and Turley U.S. Pat. No. 4,892,543. The disclosures of each of these patents are incorporated herein in their entirety by reference. Other examples of naturally actuated, shape-changing accommodating IOLs are described in co-pending, commonly assigned U.S. patent application Ser. Nos. 09/656,661, 09/657,251, and 09/657,325, all filed on Sep. 7, 2000, and in co-pending, commonly assigned U.S. patent application Ser. No. 09/855,331, filed May 15, 2001. The disclosures of each of these applications are incorporated herein in their entirety by reference.

Examples of axially movable accommodating IOLs are disclosed in Gwon et al. U.S. Pat. No. 6,176,878 and Laguette et al. U.S. Pat. No. 6,406,494. The disclosures of both these patents are incorporated herein in their entirety by reference.

IOLs which use primarily only one of the above mechanisms for accommodation have not been able to achieve the full add power required for a typical patient.

In view of the foregoing, it would be beneficial in the art, and there continues to be a need, to provide new IOLs with enhanced accommodation ability.

SUMMARY OF THE INVENTION

In accordance with the present invention, various arrangements are provided for providing IOLs with enhanced accommodation ability. The accommodation may be achieved solely through axial movement of the optic, or through a combination of one or more of axial movement, deformation, and multifocal design of the optic.

In a first broad aspect of the invention, an intraocular lens comprises a unitary optic formed of a deformable material, and an accommodation assembly coupled to the optic and structured to cooperate with the eye to effect accommodating axial movement of the optic and accommodating deformation of the optic in response to one or more naturally occurring actions of the eye. The combined axial movement and deformation is effective to provide enhanced accommodation relative to the axial movement alone or the deformation alone.

In one advantageous embodiment of the invention, the optic is an aspheric optic having progressive correction powers that vary from a baseline power for distance vision correction to an add power that is reduced relative to a power for full near vision correction, wherein the combined axial movement, deformation, and add power is effective to provide enhanced accommodation relative to the axial movement and the deformation without the add power.

In another advantageous embodiment of the invention, the optic is a multifocal optic having a first zone configured to provide distance vision correction and a second zone having an add power that is reduced relative to a power for full near vision correction, wherein the combined axial movement, deformation, and add power is effective to provide enhanced accommodation relative to the axial movement and the deformation without the add power.

In a second broad aspect of the invention, an intraocular lens comprises a unitary, deformable multifocal optic including a first zone having a baseline power for distance vision correction and a second zone having an add power, and a force transfer assembly coupled to the optic and structured to cooperate with the eye to effect deformation of the optic so as to change the power of at least one of the first and second zones. Preferably, the force transfer assembly is structured to increase the curvature of at least one of the zones in response to a compressive force exerted by the eye, thereby increasing the power of that zone. More preferably still, the force transfer assembly is also structured to axially move the optic in responsive to the compressive force exerted by the optic, wherein the axial movement of the optic combines with the increased add power obtained through the deformation to provide enhanced accommodation relative to the deformation alone.

In a third broad aspect of the invention, an intraocular lens comprises a deformable optic having progressive correction powers that vary from a baseline power for distance vision correction to a maximum add power that is reduced relative to a power for full near vision correction, and a force transfer assembly coupled to the optic and structured to cooperate with the eye to effect deformation of the optic so as to increase the maximum add power. Preferably, the force transfer assembly is also structured to axially move the optic in responsive to the compressive force exerted by the optic, wherein the axial movement of the optic combines with the increased add power obtained through the deformation to provide enhanced accommodation relative to the deformation alone. More preferably, the force transfer assembly is also structured to axially move the optic in responsive to the compressive force exerted by the optic, wherein the axial movement of the optic combines with the increased add power obtained through the deformation to provide enhanced accommodation relative to the deformation alone.

A preferred embodiment of the movement/force transfer assembly usable with the invention according to any of all of the above broad aspects comprises an outer ring surrounding the optic, and movement assembly including a plurality of intermediate members that extend between the optic and the outer ring and transmit forces therebetween. The optic preferably has a circular periphery centered on an optical axis and is adapted to focus light toward a retina of an eye and to provide a vision correction. The outer ring is spaced from the optic with voids therebetween.

The outer ring may be either circular or ovoid in configuration. In embodiments having a circular outer ring, the intermediate members are preferably distributed asymmetrically about any plane that includes the optical axis. For instance, in one preferred embodiment, three intermediate members are arranged at 120° intervals around the circumference of the ring. In embodiments having an oval outer ring, there are preferably only two diametrically opposed intermediate members.

In the case of an oval outer ring, the ring has a major axis and a minor axis. In one embodiment of the invention, the outer end of each intermediate member is secured to the outer ring at a point on the major axis, and the inner end is secured to the periphery of the optic at a point on the minor axis. In other words, the intermediate members are nonlinear, and the inner and outer ends are displaced by 90° with respect to one another. In another embodiment, the inner and outer ends are both aligned with the major axis.

Each intermediate member may have a hinge therein that permits radial forces imparted by the surrounding eye structure, e.g. muscles, to more effectively translate the optic along the optical axis. The hinges may have any suitable structure effective to provide such enhanced translation relative to a substantially identical IOL including intermediate members without hinges, such as an IOL with uniformly structured intermediate members. A typical hinge structure may include a reduced axial or circumferential thickness region along a plate-like intermediate member.

Preferably, the outer ring has an outer surface that is convexly outwardly curved to match the contour of the interface between the capsular bag and the zonules of the eye. In addition, the outer ring may have at least one relatively sharp edge to reduce epithelial cell growth thereon. In addition, the outer ring may be continuous and have an axial thickness of at least 0.4 mm. Desirably, the optic, outer ring and intermediate members are integrally formed, for example molded, of a single piece of material.

In one embodiment, the outer ring has an axial dimension and the intermediate members attach to a posterior edge of the outer ring. Furthermore, the intermediate members may be bowed in the posterior direction, causing the optic to be posteriorly vaulted.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 1 is a vertical cross-section of an eye illustrating an exemplary intraocular lens of the present invention positioned within the capsular bag;

FIG. 2 is a cross-section similar to FIG. 1 showing forward or anterior movement of an optic of the intraocular lens;

FIG. 3 is a plan view of the exemplary intraocular lens of the present invention having an oval outer ring and a pair of nonlinear intermediate members;

FIG. 4 is a plan view of an alternative intraocular lens of the present invention having two radially oriented intermediate members;

FIG. 5 is a plan view of an alternative intraocular lens of the present invention having three radially oriented intermediate members;

FIGS. 8C and 8D are side elevational and plan views, respectively, of the intraocular lens of FIG. 8A.

FIG. 9 is a view similar to FIG. 7B, showing an embodiment of the invention having an alternate hinge configuration;

FIG. 10A is an anterior plan view showing yet another embodiment of an intraocular lens according to the present invention;

FIG. 10B is a sectional view taken through line B—B of FIG. 10A; and

FIG. 10C is a sectional view taken through line C—C of FIG. 10A;

DESCRIPTION OF THE PREFERRED EMBODIMENTS

Figure 6:
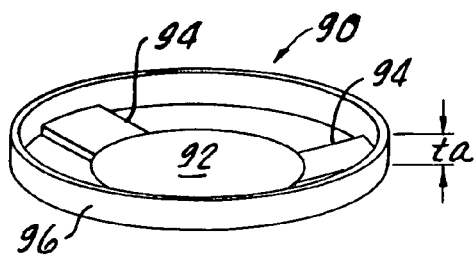
FIG. 6 is a perspective view of an alternative intraocular lens of the present invention having three radially oriented intermediate members.

Referring to the drawings in more detail, an intraocular lens (IOL) 20 according to an exemplary embodiment of the present invention is illustrated in FIGS. 1 and 2 after implantation in the capsular bag 22 of an eye. Exemplary IOL 20 includes an optic 24 and a movement assembly 26 coupled thereto. The optic 24, which has an optical axis OA, is adapted to focus light onto a retina of an eye. The movement assembly 26 of exemplary IOL 20 cooperates with the eye to effect accommodating movement of the optic 24 and, in particular, converts radial movement (i.e., movement perpendicular to the optical axis OA) of the capsular bag of an eye to axial movement (i.e., movement parallel to the optical axis OA) of the optic 24. In the exemplary embodiment, the movement assembly 26 biases the optic 24 in a posterior direction (to the right) against the posterior wall of the capsular bag 22.

A brief description of the anatomy of the eye is appropriate in order to understand the invention. The capsular bag 22 resides in the posterior chamber of the eye and is in direct contact with the jelly-like vitreous humor 28 which fills the nearly spherical space between the capsular bag and the retina (not shown). In a healthy person, the capsular bag 22 contains the natural crystalline lens which transmits light passing through the orifice of the iris 30 to the retina. The capsular bag 22 is connected to an annular ciliary muscle 34 by suspensory ligaments or zonules 36. The ciliary muscle 34 is the chief agent in accommodation, i.e., in adjusting the eye to focus on near objects. The zonules 36 retain the lens in position and are relaxed by the contraction of the ciliary muscle 34, thereby allowing a natural crystalline lens to become more convex.

Applying this anatomy to the present invention, exemplary IOL 20 is configured to facilitate movement of the optic 24 in response to the action of the ciliary muscle 34 and the zonules 36. When the ciliary muscle 34 constricts inward, the zonules 36 relax and reduce the equatorial diameter of the capsular bag 22, wherein the optic 24 translates in the posterior direction against the rear wall of the capsular bag 22. Conversely, when the ciliary muscle 34 relaxes, the zonules 36 tense and increase the equatorial diameter of the capsular bag 22, thereby moving the optic 24 in the anterior direction, or at least reducing the posterior bias.

It should be understood that, in the illustrated embodiment, the optic 24 is biased against the rear wall of the capsular bag 22 at all times, and axial movement of the optic from the action of the ciliary muscle 34 is primarily governed by the position of the rear wall. That is, changes in pressure of the vitreous humor 28 act on the rear wall of the capsular bag 22 and cause it to translate in the axial direction. This movement is facilitated by relaxation of the ciliary muscle 34, which at least reduces the rearward bias of the optic 24. For example, FIG. 2 illustrates forward movement of the optic 24 due to increase in pressure of the vitreous humor 28. One advantage of the present invention is that the optic 24 remains biased against the rear wall of the capsular bag 22 yet can accommodate substantial forward or anterior movement because of long intermediate members.

FIG. 3 illustrates the exemplary IOL 20 in plan view, wherein a generally circular periphery or peripheral edge 42 defines the radially outer extent of the optic 24 and separates a posterior face from an anterior face. The optic 24 is typically circular, but may exhibit a different shape as long as the optical correction character is centered about the optical axis OA. The optic 24 may be bi-convex, or the anterior and posterior faces can take other shapes, such as planar or concave. In any event, the posterior face and anterior face are spaced apart on opposite sides of an optic plane (not shown) that extends perpendicular to the optical axis OA. In other words, the optic 24 is centered on and oriented in the optic plane.

In a preferred embodiment, the optic 24 is a multifocal optic having a plurality of zones of varying optical powers, wherein the maximum add power of the Anear zones is reduced by an amount equivalent to the diopter shift obtained through axial movement of the optic 24. Thus, the net power correction in the near zones is equal to the patients full add prescription only when optic 24 has moved to the near distance (i.e. anteriormost) position. Examples of suitable multifocal optics are disclosed in Lang et al. U.S. Pat. No. 6,231,603 and Lang et al. PCT International Application No. WO/01/82839 A1. The disclosures of both the U.S. patent and this PCT international application are incorporated in their entireties herein by reference.

The movement assembly 26 comprises a pair of intermediate members 50a, 50b connected to and extending between the circular periphery 42 of the optic 24 and an outer ring 52. Each intermediate member 50a, 50b has an inner end 54 connected to the circular periphery 42, and an outer end 56 connected to the outer ring 52. AConnected in this sense means firmly attached to with adhesive or ultrasonic bonding, or preferably formed integrally, or as a cohesive single piece. In the latter case, the lens is desirably molded. Each intermediate member 50a, 50b is desirably oriented in a plane that is in the optic plane. Indeed, the intermediate members 50a, 50b and outer ring 52 may have approximately the same thickness and be located in the same plane.

Although controlled fibrosis (i.e., cellular growth) on the outer ring 52 may be desirable, the IOLs 20 of the invention inhibit cell growth, particularly epithelial cell growth, onto the optic 24. This is accomplished by configuring the periphery 42 of the optic 24 with mechanical barriers such as relatively sharp posterior and/or anterior edge corners. The proliferation of unwanted epithelial cell growth may also be inhibited through the use of material properties.

The intermediate members 50a, 50b of the IOL 20 are substantially longer than previous intermediate members as they extend in a nonlinear fashion from the outer ring 52 to the circular optic periphery 42. More particularly, the inner end 54 and outer end 56 are angularly spaced about the optical axis OA by at least approximately 90°. The midportion of each intermediate member 50 extends in a serpentine fashion between its inner and outer ends.

In a preferred embodiment, as seen in FIG. 3, the outer ring 52 is oval in shape and has a major axis 60 perpendicular to the optical axis OA. A minor axis 62 extends perpendicularly to the major axis 60 and to the optical axis OA. Desirably, the outer ends 56 of the intermediate members 50 connect to the oval ring 52 along the major axis 60. In this way, the length of the intermediate members 50 is maximized. In the illustrated embodiment, the inner ends 54 of the intermediate members 50 connect to the circular optic periphery 42 along the minor axis 62. Therefore, the inner and outer ends 54, 56 are angularly spaced apart by about 90°.

FIG. 4 illustrates an alternative IOL 70 of the present invention having an optic 72, an oval outer ring 74, and a pair of intermediate members 76a, 76b extending radially therebetween. Again, the optic 72, outer ring 74 and intermediate members 76a, 76b are desirably formed as a single homogeneous (i.e., integral) piece. The oval outer ring 74 is believed to move the optic 72 axially with greater effectiveness than a circular ring because of the orientation of the intermediate members 76a,b along the major axis.

The fixation members 76a,b are shown as plate-like, and desirably are greater in width (the dimension parallel to the minor axis) than axial thickness (the dimension parallel to the optical axis). Preferably, the ratio of width to axial thickness is about four. In absolute terms, the width of the fixation members 76a, 76b may be between about 0.8 mm and about 3.0 mm.

FIG. 5 illustrates a still further IOL 80 having an optic 82, an outer ring 84, and three evenly arranged and radially oriented intermediate members 86a, 86b and 86c. Because the intermediate members 86 are not symmetric about any plane through the optical axis OA, forces exerted by the surrounding capsular bag do not act in opposition to one another and thus are translated more effectively into axial movement of the optic 82. The radial thickness $t_r$ of the outer ring 84 is indicated, and is desirably in the range of 0.2–0.6 mm. Moreover, the corners, or at least one corner, of the outer peripheral edge of the outer ring 84 are desirably relatively sharp to reduce the instance of epithelial cell growth thereon.

Figure 6A:
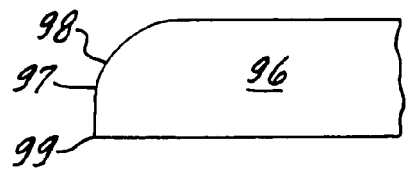
FIG. 6A is an elevational view of one edge of the intraocular lens of FIG. 6.

FIGS. 6 and 6A illustrate a still further IOL 90 having an optic 92, a plurality of intermediate members 94 extending radially outward therefrom, and an outer ring 96. The edge surface 97 of the outer ring 96 may be contoured to conform to the inner wall of the capsular bag. Therefore, as seen in FIG. 6A, at least a portion 98 of the edge surface 97 is convexly outwardly curved. At the same time, at least one corner, in this case the posterior corner 99, is left sharp (i.e. unpolished) to form a barrier against posterior capsular opacification (PCO).

Furthermore, FIG. 6 illustrates the greater axial thickness $t_a$ of the outer ring 96 with respect to the axial thickness of the intermediate members 94 and optic 92. Specifically, the axial thickness $t_a$ of the outer ring 96 is desirably between about 0.4 mm and about 1.0 mm. Without wishing to limit the invention to any particular theory of operation, it is believed that a ring having an axial thickness in this range will place both the posterior and the anterior zonules of the eye under tension. Thus, both sets of zonules work in unison to change the diameter of the capsular bag in response to action of the ciliary muscle, resulting in axial movement of the optic. A thinner ring would not interact as effectively with both sets of zonules, and thus, in all likelihood, would result in less axial movement.

In addition, an outer ring 96 having increased axial thickness will increase the pressure on the sharp corner 99 of the edge surface 97 to increase the barrier effect of the ring against PCO.

FIGS. 7A–7E show another IOL 100 of the present invention having a circular outer capsular bag support ring 102, an inner optic 104, and a movement system comprising a plurality of radially-oriented plate-like intermediate members 106 extending therebetween. Preferably, the optic 104, whether it be bi-convex or otherwise, is circumscribed by a circular rim 105 to which the fixation intermediate members 106 are directly attached. The rim 105 desirably has a constant axial dimension and helps to reduce glare while not increasing incision size.

Movement systems other than that shown may be suitable, such as a more solid interface rather than discrete intermediate members. However, separated intermediate members with voids therebetween and between the optic 104 and support ring 102 are preferred. The support ring 102, inner optic 104, and intermediate members 106 are firmly attached to each other with adhesive or ultrasonic bonding, or preferably formed integrally, i.e., molded or machined as one cohesive (homogeneous) piece of material. The IOL 100 is desirably liquid injection molded from silicone or machined from a hydrophilic material which fabrication process reduces cost and increases quality and/or consistency of the product.

Figure 7A:
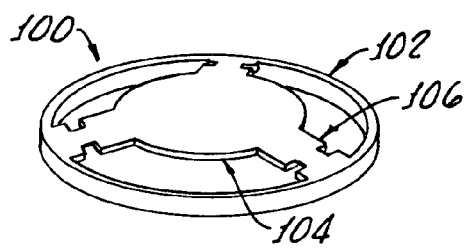
FIG. 7A is a perspective posterior view of a still further alternative intraocular lens of the present invention having three radially oriented plate-like intermediate members and an optic that is bowed slightly out of the plane of a surrounding capsular bag support ring.
Figure 7B:
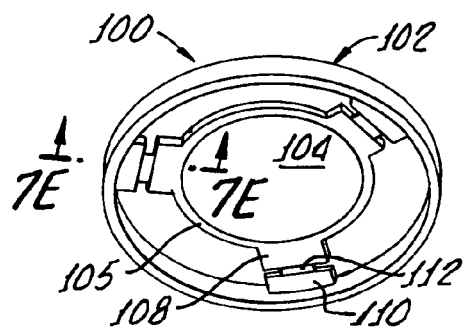
FIG. 7B is a perspective anterior view of the intraocular lens of FIG. 7A.

FIG. 7A illustrates the IOL 100 from the posterior side, while FIG. 7B is an anterior view. These two views show the axial position at which the intermediate members 106 attach to the support ring 102. That is, the support ring 102 has an axial dimension and the intermediate members 106 attach to a posterior edge thereof. When implanted, the intermediate members 106 and connected optic 104 are therefore held in a posterior-most position with respect to the support ring 102.

As in the embodiment of FIG. 6, the edge surface of the outer ring 102 is contoured to facilitate implantation within the capsular bag of the patient. More particularly, the support ring 102 has an outer surface that is convexly curved to better mate with the concave inner wall portion of the capsular bag between the anterior and posterior zonules.

Figure 7C:
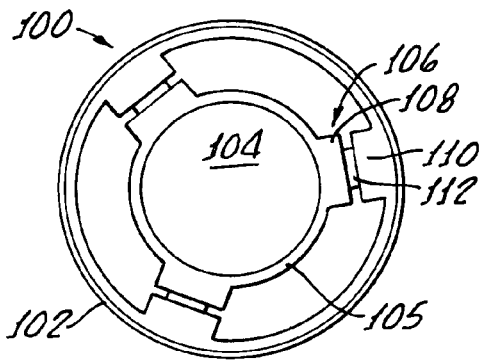
FIGS. 7C and 7D are plan and side elevational views, respectively, of the intraocular lens of FIG. 7A.
Figure 7D:
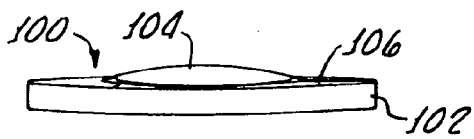
Figure 7E:
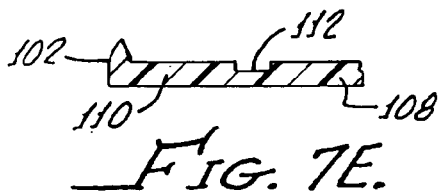
FIG. 7E is a sectional view taken through line 7E—7E of FIG. 7B.

With reference to FIGS. 7C and 7E, the intermediate members 106 comprise a radially inner portion 108, a radially outer portion 110, and a hinge 112 therebetween. The inner and outer portions 108, 110 are generally plate-like having larger circumferential dimensions then axial dimensions. The hinge 112 may be formed in a number of ways, and as illustrated comprises a region wherein both the axial and the circumferential thickness are reduced by about 50% with respect to the inner and outer portions 108, 110. The reduced material at the hinge 112 means that it is weaker than the remaining intermediate member and thus will more easily bend at that location. The location of each hinge 112 is desirably the same for all of the fixation intermediate members 106, and preferably is closer to the support ring 102 than to the optic 104. For example, each hinge 112 may be located about 60% of the way from the optic 104 to the support ring 102.

FIG. 7D illustrates the IOL 100 in elevational view wherein the support ring 102 lies substantially in a plane and the optic 104 projects in a posterior direction therefrom by virtue of the shape of the intermediate members 106. Specifically, the intermediate members 106 are bowed slightly in the posterior direction such that the optic 104 will tend to lie against or closely adjacent to the posterior wall of the capsular bag. As explained above, relaxation of the ciliary muscles surrounding the capsular bag either moves the optic 104 in the anterior direction or reduces the posterior bias imparted thereto by the intermediate members 106. As a result, the vitreous humor behind the capsular bag can move the optic 106 forward, or in the anterior direction.

In one exemplary embodiment, the support ring 102 has a diameter of between about 9.0–10.5 mm, and an axial thickness of about 0.7 mm. Furthermore, the support ring 102 has a curvature that mimics the curvature of the natural capsular bag between the anterior and posterior zonules, which curvature is between about 0.3–1.0 mm. As mentioned above, at least one corner edge of the outer ring is left sharp to help prevent cell growth thereon.

Although three radial intermediate members 106 are illustrated 120° apart, the configuration of the intermediate members 106 may vary. However, two factors that are believed to facilitate axial movement, or accommodation, of the optic 104 are the tripod orientation and presence of the hinges 112. More specifically, inward radial forces from the surrounding ciliary muscle and intermediary zonules are transmitted from the support ring 102 through the intermediate members 106 to the optic 104. Because the intermediate members 106 are oriented so that none is diametrically opposed to another, there are no directly opposing forces and a larger component therefore translates into axial movement of the optic 104.

The intermediate members 106 are plate-like to increase stability of the lens in the eye. That is, the forces imparted by the surrounding ciliary muscle may not be entirely uniform and may exert torsional forces on the lens. Plate-like intermediate members 106 help resist twisting of the lens and thus increase stability. The circumferential thickness, or width, of the intermediate members 106 may be between about 1.5–4.0 mm, and the axial thickness is desirably between about 0.2–0.5 mm.

FIG. 9 shows an alternate embodiment of an IOL 102' substantially similar to the embodiment of FIGS. 7A-7E, except that the thickness of the hinge portion 112' is reduced in the axial direction only. That is, the circumferential thickness, or width, of each plate-like intermediate member 106' is uniform throughout its length. This hinge configuration has been found to be less susceptible to fibrosis than a hinge configuration having reduced thickness in the circumferential direction.

Another alternative IOL 120 of the present invention is seen in FIGS. 8A–8D. As in an earlier embodiment, there are only two intermediate members 122 extending between an oval shaped outer capsular bag support ring 124 and an inner circular optic 126. In the illustrated embodiment, the outer ring 124 comprises a band having a generally rectangular cross-section with a longer axial than radial dimension. Preferably, at least one corner of the outer ring 124 is sharp to prevent epithelial cell growth thereon. The support ring 124, inner optic 126, and intermediate members 122 are firmly attached to each other with adhesive or ultrasonic bonding, or preferably formed integrally, i.e., molded or machined as a cohesive single piece. The IOL 120 is desirably liquid injection molded from silicone or machined from a hydrophilic material which, again, reduces cost and increases quality and/or consistency of the product.

As seen best in FIG. 8D, the oval outer ring 124 has a major axis 121 and a minor axis 123, and the two intermediate members 122 are diametrically opposed across the optic 126 along the major axis 123. In one exemplary embodiment, the support ring 124 has a major diameter of between about 115–135% of the minor diameter.

The intermediate members 122 are plate-like, each having a relatively larger circumferential than axial dimension. In contrast to the IOL 100 of FIGS. 7A–7D, the intermediate members 122 lie in a plane defined by the oval-shaped outer ring 124, and thus the optic 126 is not bowed either way. Furthermore, the intermediate members 122 are joined to the inner surface of the outer ring 124 at approximately the axial midpoint thereof. Therefore, in contrast to the earlier embodiment, the optic 126 is not positioned or biased to favor movement in one direction or the other.

Figure 8A:
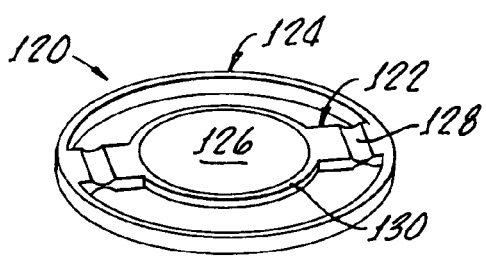
FIG. 8A is a perspective view of a still further alternative intraocular lens of the present invention having two radially oriented plate-like intermediate members connecting a central optic to an oval surrounding capsular bag support ring.
Figure 8B:
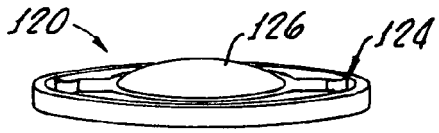
FIG. 8B is another perspective view of the intraocular lens of FIG. 8A.

With reference to FIG. 8A, each intermediate member 122 has a hinge 128 therein located closer to the outer ring 124 than to the optic 126. The location of each hinge 128 is desirably the same for all of the intermediate members 122, and preferably is located about 75% or more of the way from the optic 126 to the support ring 124. Empirical determination of hinge 128 location optimizes the design such that less radial and axial compression force is required to axially translate the optic 126, while at the same time the ability of the lens to resist twisting is not adversely affected. In the illustrated embodiment, these hinges 128 are formed by reduced axial thickness portions along each intermediate member 122. For example, curved troughs on both sides of intermediate members 122 as shown may form the hinges. Alternatively, or in addition, the circumferential dimension of each intermediate member 122 may be reduced.

As with the earlier embodiment, the optic 126, whether it be biconvex or otherwise, is recessed from a circular rim 130 to which the intermediate members 122 are directly attached. The rim 130 is slightly tapered downward toward the optic and helps reduce glare on the lens. Desirably, the maximum axial dimension of the rim 130 is greater than the center thickness of the optic 126. Advantageously, a reduced center thickness permits a reduction in incision size.

FIGS. 10A–10C show an alternate embodiment of an IOL 120' similar to the embodiment of FIGS. 8A-8D, except that the optic 126' is multifocal, and oval support ring 124' has a non-uniform cross-sectional area. Specifically, the radial thickness of the support ring 124' increases from a minimum value $t_{r1}$, for instance about 0.2 mm, at diametrically opposed locations 125a and 125b along the minor axis 121', to a maximum value $t_{r2}$, for instance about 0.6 mm, at diametrically opposed locations along the major axis 123', where the intermediate members 122' are secured to the ring 124'. In addition, the axial thickness $t_a$ of the ring 124' is constant throughout the entire circumference of the ring 124' and has a value greater than the maximum radial thickness $t_{r2}$.

The circumferential thickness, or width, of each intermediate member 122' is also non-uniform throughout its length, for instance decreasing in a non-linear fashion from a maximum width where the intermediate member 122' joins the circular rim 130' of the optic 126' to a minimum width at the hinge 128', and remaining substantially constant between the hinge 128' and the outer ring 124'. This particular configuration of the oval outer ring 124' and intermediate members 122' has been found to be particularly stable, with minimal "flopping", twisting, or other unwanted movement, of the thinnest portions 125a and 125b of the ring 124'.

A series of tests were run on a prototype IOL in order to evaluate the performance of the IOL under compression. The prototype IOL had the configuration of IOL 120' shown in FIG. 10 and was formed entirely of a unitary, reinforced cross-linked silicone polymeric material of the type described in Christ U.S. Pat. Nos. 5,236,970, 5,376,694, 5,494,946, 5,661,195, 5,869,549, and 6,277,147. The disclosures of each of these U.S. patents are incorporated in their entirety herein by reference.

During the tests, it was observed that, when the IOL 120' was compressed an amount in the range of about 0.3 mm to about 1 mm, the image quality in the far zone 132 improved slightly, while the image quality in the near zone (add power=2D), decreased slightly.

Figure 11:
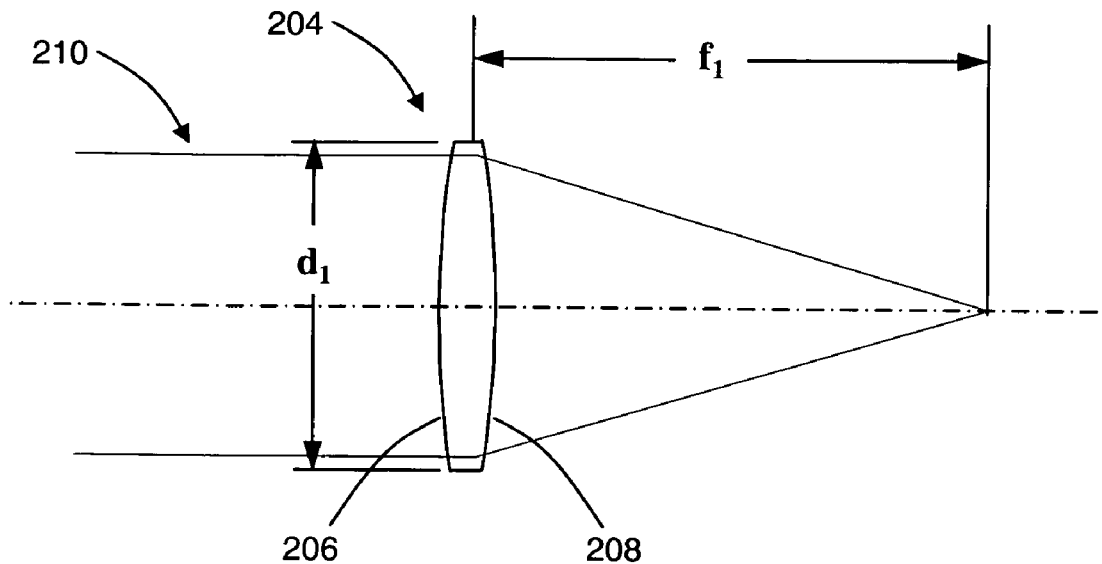
FIGS. 11 and 12 are side elevational views of an equiconvex optic.
Figure 12:
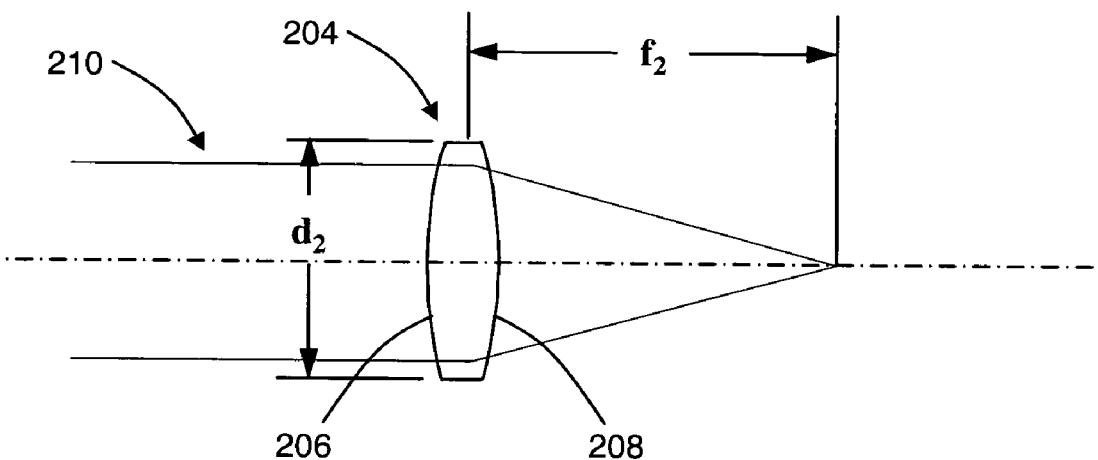

Referring to FIGS. 11 and 12, in certain embodiments, an equiconvex optic 204 comprises surfaces 206, 208. Those of skill in the art will recognize that the optic 204 may be characterized by a focal length f (e.g., $f_1$ in FIG. 11 and $f_2$ in FIG. 12) produced as light 210 is refracted by the surfaces 206, 208. It will also be recognized by those of skill in the art that the diopter power D of the equiconvex optic 204 is equal to 1/f, when f is in units of meters. For isotropic compression (e.g., $d_1$, $d_2$ in FIGS. 11 and 12, respectively) or deformation (e.g., deformation of the surfaces 206, 208 illustrated in FIGS. 11 and 12) of the equiconvex optic 204, there exists a relationship between the amount of diametric compression d (i.e. decrease in refractive zone size; for example $d_1-d_2$) and the increase in diopter power (for example $D_2-D_1$). With an increase in diopter power (e.g., from $D_1$ to $D_2$,) at least some improvement in near vision can be expected. Referring again to FIG. 10, by combining the increased diopter power obtained through deformation of the optic 126' with that obtained through axial movement, it is believed that enhanced accommodation can be achieved. In other words, a patient's presbyopia can be effectively reduced. Still better accommodation, or further reduction of presbyopia, can be obtained from the add power in the near zone 134 of a multifocal optic 126', or from the maximum add power of an aspheric optic.

Although the aforementioned tests were performed on an IOL 120' formed of a reinforced cross-linked silicone polymeric material, the principles of the invention will apply equally well to accommodating IOLs formed of any ophthalmically acceptable, deformable material or combination of materials. For instance, one or more of the optic 126', intermediate members 122', and outer ring 124' may be formed of an acrylic polymeric material. Particularly useful materials and combinations of materials are disclosed in patent application Ser. No. 10/314,069, filed Dec. 5, 2002.

Furthermore, while each of the accommodation assemblies illustrated herein comprises an outer ring surrounding and spaced from the optic with voids therebetween, and a plurality of intermediate members extending between and connecting the optic and the outer ring, these assemblies are merely exemplary. Other assembly configurations capable of effecting both axial movement and accommodating deformation of the optic are also included within the scope of the invention. For instance, accommodation and/or force transfer assemblies of the type shown in the aforementioned co-pending, commonly assigned U.S. patent application Ser. Nos. 09/656,661, 09/657,251, and 09/657,325, may also be suitable.

While the present invention has been described with respect to various specific examples and embodiments, it is to be understood that the invention is not limited thereto and that it can be variously practiced within the scope of the following claims.

What is claimed is:

1. An intraocular lens for insertion into an eye, comprising:
    a unitary, deformable multifocal optic including a first zone having a baseline power for distance vision correction and a second zone having an add power; and
    a continuous outer ring surrounding the optic and spaced therefrom, the continuous outer ring configured for implantation within a capsular bag of an eye; and
    a force transfer assembly comprising a plurality of intermediate members extending between and connecting the optic and the outer ring;
    wherein the force transfer assembly is coupled to the optic and structured to cooperate with the eye to effect deformation of the optic so as to change the power of at least one of the first and second zones.

2. The intraocular lens according to claim 1, wherein the force transfer assembly is structured to change the curvature of at least one of the zones in response to a compressive force exerted by the eye.

3. The intraocular lens according to claim 2, wherein the force transfer assembly is structured to increase the curvature of at least one of the zones in response to a compressive force exerted by the eye.

4. The intraocular lens according to claim 1, wherein the force transfer assembly is structured to cooperate with the eye to effect deformation of the first zone so as to increase the baseline power.

5. The intraocular lens according to claim 1, wherein the force transfer assembly is further structured to axially move the optic in response to an action of the eye, wherein the axial movement of the optic combines with the increased add power obtained through the deformation to provide enhanced accommodation relative to the deformation alone.

6. An intraocular lens for insertion into a capsular bag of an eye, comprising:
    a deformable optic having a periphery and centered about an optical axis, the optic adapted to focus light toward a retina of an eye; and
    an accommodation assembly coupled to the optic, comprising:
        an outer ring surrounding the optic and spaced therefrom, the outer ring configured for implantation within a capsular bag of an eye; and
        at least three intermediate members extending between and connecting the optic and the outer ring;
    wherein each intermediate member of the at least three intermediate members comprises a hinge.

7. The intraocular lens according to claim 6, wherein each hinge is located closer to the outer ring than to the optic.

8. An intraocular lens for insertion into a capsular bag of an eye, comprising:
    a deformable optic having a periphery and centered about an optical axis, the optic adapted to focus light toward a retina of an eye; and
    an accommodation assembly coupled to the optic, comprising:
        an outer ring surrounding the optic and spaced therefrom, the outer ring configured for implantation within a capsular bag of an eye; and
        at least three intermediate members extending between and connecting the optic and the outer ring;
    the deformable optic has a baseline power for distance vision correction and a maximum add power that is reduced relative to a power for full near vision correction; and
    the accommodation assembly is structured to cooperate with the eye to effect deformation of the optic so as to increase the maximum add power.

9. The intraocular lens according to claim 8, wherein the optic has progressive vision powers that vary from the baseline power to the maximum add power.

10. The intraocular lens according to claim 9, wherein the accommodation assembly is structured to deform the optic so as to increase the maximum add power in response to compressive forces exerted by the eye.

11. The intraocular lens according to claim 10, wherein the accommodation assembly is further structured to cooperate with the eye to axially move wherein the axial movement of the optic combines with the maximum add power obtained through deformation to provide enhanced accommodation relative to the deformation alone.

12. An intraocular for insertion into a capsular bag of an eye, comprising:
   a deformable optic having a periphery and centered about an optical axis, the optic adapted to focus light toward a retina of an eye; and
   an accommodation assembly coupled to the optic, comprising:
      an outer ring surrounding the optic and spaced therefrom, the outer ring configured for implantation within a capsular bag of an eye; and
      at least three intermediate members extending between and connecting the optic and the outer ring;
   wherein the optic is a multifocal optic having a first zone configured to provide distance vision correction and a second zone having an add power that is reduced relative to a power for full near power correction, the combined axial movement, deformation, and add power is effective to provide enhanced accommodation relative to the axial movement and the deformation without the add power.

13. An intraocular for insertion into a capsular bag of an eye, comprising:
   a deformable optic having a periphery and centered about an optical axis, the optic adapted to focus light toward a retina of an eye; and
   an accommodation assembly coupled to the optic, comprising:
      an outer ring surrounding the optic and spaced therefrom, the outer ring configured for implantation within a capsular bag of an eye; and
      at least three intermediate members extending between and connecting the optic and the outer ring;
   wherein the optic is an aspheric optic.

14. The intraocular lens of claim 13, wherein the aspheric optic has progressive correction powers that vary from a baseline power for distance vision correction to an add power.

15. The intraocular lens of claim 14, wherein the add power that is reduced relative to a power for full near vision correction.

16. An intraocular lens for insertion into a capsular bag of an eye, comprising:
   a deformable optic having a periphery and centered about an optical axis, the optic adapted to focus light toward a retina of an eye; and
   an accommodation assembly, comprising:
      a continuous outer ring surrounding the optic and spaced therefrom, the outer ring configured for implantation within a capsular bag of the eye; and
      a plurality of intermediate members extending between and connecting the optic and the outer ring;
   wherein the accommodation assembly is structured to cooperate with the eye to effect deformation of the optic;
   wherein each intermediate member of the plurality of intermediate members comprises a hinge.

17. The intraocular lens according to claim 16, wherein each hinge is located closer to the outer ring than to the optic.

18. An intraocular lens for insertion into a capsular bag of an eye, comprising:
   a deformable optic having a periphery and centered about an optical axis, the optic adapted to focus light toward a retina of an eye; and
   an accommodation assembly, comprising:
      a continuous outer ring surrounding the optic and spaced therefrom, the outer ring configured for implantation within a capsular bag of the eye; and
      a plurality of intermediate members extending between and connecting the optic and the outer ring;
   wherein the accommodation assembly is structured to cooperate with the eye to effect deformation of the optic;
   the deformable optic has a baseline power for distance vision correction and a maximum add power that is reduced relative to a power for full near vision correction; and
   the accommodation assembly is structured to cooperate with the eye to effect deformation of the optic so as to increase the maximum add power.

19. The intraocular lens according to claim 18, wherein the optic has progressive vision powers that vary from the baseline power to the maximum add power.

20. The intraocular lens according to claim 18, wherein the accommodation assembly is structured to deform the optic so as to increase the maximum add power in response to compressive forces exerted by the eye.

21. The intraocular lens according to claim 20, wherein the accommodation assembly is further structured to cooperate with the eye to axially move wherein the axial movement of the optic combines with the maximum add power obtained through deformation to provide enhanced accommodation relative to the deformation alone.

22. An intraocular lens for insertion into a capsular bag of an eye, comprising:
   a deformable optic having a periphery and centered about an optical axis, the optic adapted to focus light toward a retina of an eye; and
   an accommodation assembly, comprising:
      a continuous outer ring surrounding the optic and spaced therefrom, the outer ring configured for implantation within a capsular bag of the eye; and
      a plurality of intermediate members extending between and connecting the optic and the outer ring;
   wherein the accommodation assembly is structured to cooperate with the eye to effect deformation of the optic;
   wherein the optic is a multifocal optic having a first zone configured to provide distance vision correction and a second zone having an add power that is reduced relative to a power for full near power correction, the combined axial movement, deformation, and add power is effective to provide enhanced accommodation relative to the axial movement and the deformation without the add power.

23. An intraocular lens for insertion into a capsular bag of an eye, comprising:
   a deformable optic having a periphery and centered about an optical axis, the optic adapted to focus light toward a retina of an eye; and an accommodation assembly, comprising:
  a continuous outer ring surrounding the optic and spaced therefrom, the outer ring configured for implantation within a capsular bag of the eye; and
  a plurality of intermediate members extending between and connecting the optic and the outer ring;
wherein the accommodation assembly is structured to cooperate with the eye to effect deformation of the optic;
wherein the optic is an aspheric optic.

24. The intraocular lens of claim 23, wherein the aspheric optic has progressive correction powers that vary from a baseline power for distance vision correction to an add power.

25. The intraocular lens of claim 24, wherein the add power that is reduced relative to a power for full near vision correction.

26. An intraocular lens for insertion into a capsular bag of an eye, comprising:
  a deformable optic having a periphery and centered about an optical axis, the optic adapted to focus light toward a retina of an eye; and
  an accommodation assembly, comprising:
    a continuous outer ring surrounding the optic and spaced therefrom, the outer ring configured for implantation within a capsular bag of the eye; and
    a plurality of intermediate members extending between and connecting the optic and the outer ring;
  wherein the accommodation assembly is structured to cooperate with the eye to effect deformation of the optic;
  wherein the plurality of intermediate members are oriented so that none of the intermediate members is diametrically opposed to any of the remaining intermediate members.

* * * * *